(12) United States Patent
Adams

(10) Patent No.: US 6,649,617 B1
(45) Date of Patent: Nov. 18, 2003

(54) TREATMENT FOR STROKE MANAGEMENT

(75) Inventor: Jerry Leroy Adams, Wayne, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/806,289

(22) PCT Filed: Oct. 6, 1999

(86) PCT No.: PCT/US99/23274

§ 371 (c)(1),
(2), (4) Date: Mar. 27, 2001

(87) PCT Pub. No.: WO00/19824

PCT Pub. Date: Apr. 13, 2000

Related U.S. Application Data

(60) Provisional application No. 60/103,320, filed on Oct. 7, 1998.

(51) Int. Cl.[7] .............................................. A61K 31/505
(52) U.S. Cl. ...................................................... 514/256
(58) Field of Search ......................................... 514/256

(56) References Cited

U.S. PATENT DOCUMENTS

| | | |
|---|---|---|
| 5,776,954 A | 7/1998 | Laszlo et al. |
| 5,792,778 A | 8/1998 | Laszlo et al. |
| 6,096,739 A | 8/2000 | Feuerstein |

FOREIGN PATENT DOCUMENTS

| | | |
|---|---|---|
| WO | WO 97/05877 | 2/1997 |
| WO | WO 97/05878 | 2/1997 |
| WO | WO 97/12876 | 4/1997 |
| WO | WO 97/16426 | 5/1997 |
| WO | WO 97/16441 | 5/1997 |
| WO | WO 97/16442 | 5/1997 |
| WO | WO 97/35855 | 10/1997 |
| WO | WO 97/35856 | 10/1997 |
| WO | WO 97/47618 | 12/1997 |
| WO | WO 98/21957 | 5/1998 |
| WO | WO 98/47892 | 10/1998 |
| WO | WO 98/47899 | 10/1998 |
| WO | WO 98/52937 | 11/1998 |
| WO | WO 98/52940 | 11/1998 |
| WO | WO 98/52941 | 11/1998 |
| WO | WO 99/01449 | 1/1999 |
| WO | WO 99/03837 | 1/1999 |
| WO | WO 99/20624 | 4/1999 |

*Primary Examiner*—Theodore J. Criares
(74) *Attorney, Agent, or Firm*—Dara L. Dinner; Theodore R. Furman; Charles M. Kinzig

(57) ABSTRACT

A method of treating a CNS injury to the brain, in a mammal in need of treatment, which comprises administering to said mammal an effective amount of a cytokine suppressive binding protein compound of formula I

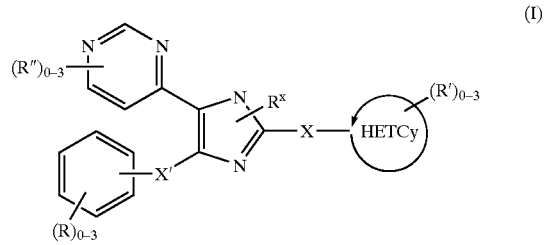

wherein the radicals are defined herein.

15 Claims, No Drawings

TREATMENT FOR STROKE MANAGEMENT

Applicant claims the benefit of Provisional application No. 60/103,320 filed Oct. 7, 1998.

FIELD OF THE INVENTION

This invention relates to the novel use of imidazole compounds in the treatment of stroke and stroke management.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock, syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutrophil attractant/activation protein-1(NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for the treatment, and for the prevention of CNS injuries which are related to the ability of compounds which are cytokine suppressive, i.e. compounds which are capable of inhibiting cytokines, such as IL-1, IL-6, IL-8 and TNF.

SUMMARY OF THE INVENTION

This invention relates to the use of substituted imidazole compounds, or pharmaceutical compositions thereof in the treatment of stroke, and stroke management.

The compounds for use herein are described in PCT [US97/09888 filed Jun. 6, 1997, and published Dec. 18, 1997 as WO 97/47618, Liverton et al., now U.S. Pat. No. 5,859,041 granted Jan. 12, 1999, whose disclosures are incorporated herein by reference in their entirety.

DETAILED DESCRIPTION OF THE INVENTION

The present invention is to the novel use of the compounds described in WO 97/47618 for the treatment, an acute setting, as well as including prophylactic use, in preventing in those individuals deemed susceptible to, various CNS injuries.

Synthetic chemistry, dosages, and methods of making pharmaceutical formulations thereof are also contained within the noted patent application.

Another aspect of the present invention relates to the novel use of compounds described in WO 98/47899 (PCT/US98/07831), Dodd et al., for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 98/52937 (PCT/US98/10807), Anantanarayan et al., now U.S. Pat. No. 5,932,576, granted Aug. 3, 1999; U.S. Pat. No. 6,0874,96, and U.S. Pat. No. 6,335,336 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent and patent application.

Another aspect of the present invention relates to the novel use of compounds described in WO 99/03837 (PCT/US98/13419), Wachter et al., now U.S. Pat. No. 6,040,320 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 98/47892 (PCT/US98/07910), Beers et al., now U.S. Pat. No. 5,965,583 and U.S. Pat. No. 6,214,830 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 99/01449 (PCT/EP98/03930), Revesz et al., now U.S. Pat. No. 6,300,347 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 98/52941 (PCT/US98/11684), Hanson et al., now U.S. Pat. No. 6,087,381 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 98/52941 (PCT/US98/11684), Hanson.et al., for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 97/05878 (PCT/US96/12922), De Laszlo et al;, now U.S. Pat. No. 5,837,719, granted Nov. 17, 1998, for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent and patent application.

Another aspect of the present invention relates to the novel use of compounds described in WO 97/16441 (PCT/US96/17324), De Laszlo et al., for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 98/21957 (PCT/US97/21019), Chang et al., now U.S. Pat. No. 5,955,480 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 97/12876 (PCT/US96/15880), now U.S. Pat. No. 5,717,100, granted Feb. 10, 1998, Selnick et al., and U.S. Pat. No. 6,083,949 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 97/16426 (PCT/US96/17477), De Laszlo et al., for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 97/05877 (PCT/US96/12917), De Laszlo et al., now U.S. Pat. No. 5,782,778, granted Aug. 11, 1998, for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 97/16442 (PCT/US96/18539), De Laszlo et al., for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 98/52940 (PCT/US98/10436), Anantanarayan et al., now U.S. Pat. No. 6,423,713 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

Another aspect of the present invention relates to the novel use of compounds described in WO 99/20624 (PCT/EP98/06472) Cheng et al., now U.S. Pat. No. 6,316,464, U.S. Pat. No. 6,479,507 for the treatment, an acute setting, as well as including prophylactic use, in preventing in those individuals deemed susceptible to, various CNS injuries. Synthetic chemistry, dosages, and methods of making pharmaceutical formulations thereof are also contained within the noted patent application.

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

In addition to the advantage of using a compound which is an inhibitor of cytokine suppressive binding protein activity (CSBP) for the inhibition of IL-1 or TNF alone which is neuroprotective, inhibition of both cytokines provides for increased efficacy. These compounds may also be useful for all types of strokes, regardless of the thrombotic/hemorrhagic variants. This would allow for early intervention, possible without use of CAT scans, and potential use in conjugation with tPA, or streptokinase, for instance.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., Stoke, Vol. 25.; No. 7, pp. 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

As noted, these compounds are useful as cytokine inhibitors, and in particular the preferred method of inhibition is the inhibition of the CSBP/p38/RK kinase pathway. A description of the assay for inhibition of the cytokine specific binding protein (CSBP) is also found in WO 95/07922, whose disclosure is incorporated by reference in its entirety, as well as in U.S. Pat. No. 5,777,097. A kinase binding assay is also described herein. Updated versions of a CSBP kinase assay may be found in later filed SB patent applications including WO 98/57966 for instance.

The compounds of WO 97/47618 can be used in the manufacture of a medicament for the prophylactic or therapeutic treatment of any disease state in a human, or other mammal, which is exacerbated or caused by a neurotraumatic event, such as closed head injuries.

In addition, the compounds of WO 99/20624, WO 98/52940, WO 97/16442, WO 97/05877, WO 97/16426, WO 97/12876, WO 98/21957, WO 97/16441, WO 97/05878, WO 98/52941, WO 99/01449, WO 98/47892, WO 99/03837, WO 98/52937, and WO 98/47899, can be used in the manufacture of a medicament for the prophylactic or therapeutic treatment of any disease state in a human, or other mammal, which is exacerbated or caused by a neurotraumatic event, such as closed head injuries.

The compounds of these patent applications are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides for a method of treating a neurotraumatic disease, in a mammal in need thereof, which method comprises administering to said mammal an effective amount of a CSAID™, cytokine suppressive inhibitory compound, wherein the compound is an inhibitor of the CSBP/p38/RK kinase.

As used herein, the term "inhibiting the production of IL-1 (IL-6, IL-8 or TNF)" refers to:

a) a decrease of excessive in 3in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

A new member of the MAP kinase family, alternatively termed CSBP, p38, or RK, has been identified, See Lee et al., Nature, Vol. 300 n(72), 739–746 (1994). Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses.

The invention will now be described by reference to the following biological examples which are merely illustrative and are not to be construed as a limitation of the scope of the present invention.

In vivo TNF Assay:

(1) Griswold et al., Drugs Under Exp. and Clinical Res., XIX (6), 243–248 (1993); or (2) Boehm, et al., Journal Of Medicinal Chemistry 39, 3929–3937 (1996) whose disclosures are incorporated by reference herein in their entirety.

LPS-induced TNFα Production in Mice and Rats

In order to evaluate in vivo inhibition of LPS-induced TNFα production in rodents, both mice and rats are injected with LPS.

Mouse Method,

Male Balb/c mice from Charles River Laboratories are pretreated (30 minutes) with compound or vehicle. After the 30 min. pretreat time, the mice are given LPS (lipopolysaccharide from *Esherichia coli* Serotype 055–85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055–85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels are measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polygonal rabbit antimurine TNFa (Genzyme) as the second antibody. For detection, a peroxidase-conjugated goat anti-rabbit antibody (Pierce, Rockford, Ill.) is added, followed by a substrate for peroxidase (1 mg/ml orthophenylenediamine with 1% urea peroxide). TNFα levels in the plasma samples from each animal are calculated from a standard curve generated with recombinant murine TNFα (Genzyme).

LPS-Stimulated Cytokine Production in Human Whole Blood

Assay: Test compound concentrations are, prepared at 10×concentrations and LPS prepared at 1 ug/ml (final conc. of 50 ng/ml LPS) and added in 50 uL volumes to 1.5 mL eppendorf tubes. Heparinized human whole blood is obtained from healthy volunteers and is dispensed into eppendorf tubes containing compounds and LPS in 0.4 mL volumes and the tubes incubated at 37 C. Following a 4 hour incubation, the tubes are centrifuged at 5000 rpm for 5 minutes in a TOMY microfuge, plasma is withdrawn and frozen at −80 C.

Cytokine measurement: IL-1and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP/p38 Kinase Assay:

This assay measures the CSBP/p38-catalyzed transfer of $^{32}P$ from $[a-^{32}P]ATP$ to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSBP Kinase", BioOrganic & Medicinal Chemistry, 1997, 5, 49–64).

Reactions are carried in round bottom 96 well plate (from Corning) in a 30 ml volume. Reactions contained (in final concentration): 25 mM Hepes, pH 7.5; 8 mM $MgCl_2$; 0.17 mM ATP (the $Km_{[ATP]}$ of p38 (see Lee et al., Nature 300, n72 pg. 639–746 (December 1994)); 2.5 uCi of [g-32P]ATP; 0.2 mM sodium orthovanadate; 1 mM DTT; 0.1% BSA; 10% glycerol; 0.67 mM T669 peptide; and 2–4 nM of yeast-expressed, activated and purified p38. Reactions are initiated by the addition of [gamma-32P]Mg/ATP, and incubated for 25 min. at 37° C. Inhibitors (dissolved in DMSO) are incubated with the reaction mixture on ice for 30 minutes prior to adding the 32P-ATP. Final DMSO concentration was 0. 16%. Reactions are terminated by adding 10 ul of 0.3 M phosphoric acid, and phosphorylated peptide is isolated from the reactions by capturing it on p81 phosphocellulose filters. Filters are washed with 75 mM phosphoric acids, and incorporated 32P was quantified using beta scintillation counter. Under these conditions, the specific activity of p38 is about 400–450 pmol/pmol enzyme, and the activity linear for up to 2 hr of incubation. The kinase activity values are obtained after subtracting values generated in the absence of substrate which are 10–15% of total values.

Prostoglandin Endoperoxide Synthase-2 (PGHS-2)assay:

This assay describes a method for determining the inhibitory effects of compounds of Formula (1) on human PGHS-2 protein expression in LPS stimulated human monocytes. A suitable assay for PGHS-2 protein expression may be found in a number of publications, including U.S. Pat. No. 5,593, 992 whose disclosure is incorporated herein by reference.

TNF-a in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-b mRNA

This assay characterizes the regional expression of interleukin- 1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Evaluation of compounds in specific models for rat focal Ischemic Stroke injury, may be determined by techniques well known to the skilled artisan, as described in some of the publications below. Alternatively, using microsurgical electrocoagulation of the middle cerebral artery under stereotaxic control, a suitable candidate compound is administered by either intravenous, or oral administration. Pose 24 hours of MCAO, the neurological deficits and stained forebrain sections are evaluated. Suitable endpoints are 1) neurological deficits in the forelimb, and hindlimb; 2) infact volume of (mm3); and hemispheric infarct (%; normalized to normal contralateral hemisphere).

Additional publication which are of value in this invention include, Barone et al., Stroke, 28:6, 1233–1244 (1997); Stroke, 23:9, 1337–1347 (1997); Stroke, 25:7, 1481–1488 (1994); Stroke, 24:11, 1746–51 (1993); Stroke, 28:1, 155–162 (1997); Stroke 26:9, 1665–1669 (1995); Cerebrovascular & Brain Metabolism Reviews, 6:4, 341–360 (1994); Brain Research Bulletin, 35:4, 387–392 (1994); Brain Research Bulletin, 31: 565–572 (1993); J. Cerberal Blood Flow and Metabolism, 16:3, 260–366 (1996); Neuroscience and Biobehavioral Reviews, 20:3, 445–452 (1996); Cerebrovascular Diseases: 19th Princeton Stroke Conference, Ed. Moskowitz et al., Boston: Butterworth-Heinemann Press, Chapter 7, pp. 75–91 (1995); Immunotherapy in Neuroimmunologic Diseases, Editors, Zhang et al., Martin Dunitz, Ltd. 1998 (pp. 155–174); Molecular and Chemical Neuropathy, 24: 13–30 (1995); Annals of N.Y. Academy of Sciences, Vol. 825 (1997), Neuroprotective Agents, 3rd International Conference, Editors, Slikker et al., p. 179–193.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method of treating a CNS injury to the brain, in a mammal in need of such treatment, which method comprises administering to said mammal an effective amount of a cytokine suppressive binding protein compound represented by the formula:

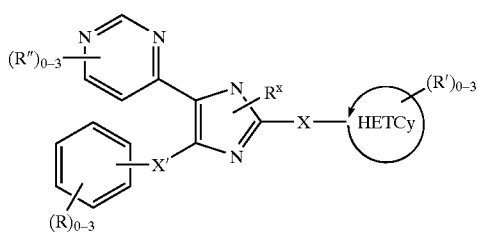

(I)

or a pharmaceutically acceptable salt thereof, wherein:

X and X' each independently represent $-(CH_2)_m-Y-(CH_2)_n-$, wherein m and n represent integers within the range of from 0–4, such that the sum of m and n is from 0–6; Y represents a member selected from the group consisting of: a direct bond; O; $S(O)_y$, with y equal to 0, 1 or 2; $NR^{q'}$, with $R^{q'}$ as defined below; C(O); OC(O); C(O)O; $SO_xNR^{q'}$ with x equal to 1 or 2 and $R^{q'}$ as defined below; $NR^{q'}SO_x$; $C(O)NR^{q'}$ and $NR^{q'} C(O)$;

represents a 4 to 10 membered non-aromatic heterocycle containing at least one N atom, and optionally containing 1–2 additional N atoms and 0–1 O or S atom;

$R^x$ represents H, $C_{1-6}$alkyl$(R^q)_3$, $C_{3-8}$cycloalkyl, $OC_{1-6}$alkyl$(R^q)_3$ or $C(O)C_{1-6}$alkyl$(R^q)_3$;

each R independently represents a member selected from the group consisting of: halo; hydroxy; $C_{1-6}$alkyl$(R^q)_3$; $OC_{1-6}$alkyl$(R^q)_3$; $C_{3-8}$cycloalkyl$(R^q)_3$; CN; $CONH_2$; $CONHC_{1-6}$alkyl$(R^q)_3$; $CON(C_{1-6}$alkyl$(R^q)_3)_2$; $NH_2$; $NHC_{1-6}$alkyl$(R^q)_3$; $NHC_{3-8}$cycloalkyl; $N(C_{1-6}$alkyl$(R^q)_3)_2$; $CON(C_{3-8}$cycloalkyl)$(C_{1-6}$alkyl$(R^q)_3)$; $CO_2H$; $CO_2C_{1-6}$alkyl$(R^q)_3$; $C(O)C_{1-6}$alkyl$(R^q)_3$; aryl$(R^q)_3$; heterocyclyl$(R^q)_3$; heteroaryl$(R^q)_3$; $CF_3$; SH; $NO_2$; $NHSO_2C_{1-6}$alkyl$(R^q)_3$; $NHSO_2$ aryl$(R^q)_3$, $NHSO_2$ heteroaryl$(R^q)_3$; $N(R^q)C(O)$ $C_{1-6}$alkyl$(R^q)_3$; $NR^{q'}C(O)NH(C_{1-6}$alkyl$(R^q)_3)$; $C_{2-4}$alkenyl$(R^q)_{2-3}$ and $C_{2-4}$alkynyl$(R^q)_{1-3}$;

each R" independently represents a member selected from the group consisting of: halo; hydroxy; C $C_{1-6}$alkyl $(R^q)_3$; $OC_{1-6}$alkyl$(R^q)_3$; $C_{3-8}$cycloalkyl$(R^q)_3$; CN; $CONH_2$; $CONHC_{1-6}$alkyl$(R^q)_3$; $CON(C_{1-6}$alkyl$(R^q)_3)_2$; $NH_2$; $NHC_{1-6}$alkyl$(R^q)_3$; $NHC_{3-8}$cycloalkyl; $N(C_{1-6}$alkyl$(R^q)_3)_2$; $CON(C_{3-8}$cycloalkyl)$(C_{1-6}$alkyl$(R^q)_3)$; $CO_2H$; $CO_2C_{1-6}$alkyl$(R^q)_3$; $C(O)C_{1-6}$alkyl$(R^q)_3$; aryl$(R^q)_3$; heterocyclyl$(R^q)_3$; heteroaryl$(R^q)_3$; $CF_3$; SH; $NO_2$; $SO_y$ $C_{1-6}$alkyl$(R^q)_3$, with y as defined above; $SO_2NH_2$; $SO_2NHC_{1-6}$alkyl$(R^q)_3$; $SO_2N(C_{1-6}$alkyl$(R^q)_3)_2$; $NHSO_2C_{1-6}$alkyl$(R^q)_3$; $NHSO_2$aryl$(R^q)_3$, $NHSO_2$ heteroaryl$(R^q)_3$; $N(R^q)C(O)C_{1-6}$alkyl$(R^q)_3$; $NR^{q'}C(O)NH(C_{1-6}$alkyl$(R^q)_3)$; $C_{2-4}$alkenyl$(R^q)_{2-3}$ and $C_{2-4}$alkynyl$(R^q)_{1-3}$;

each R' independently represents a member selected from the group consisting of: $CONH_2$; $CONHC_{1-6}$alkyl$(R^q)_3$3; $CON(C_{1-6}$alkyl$(R^q)_3)_2$; $CONHC_{3-8}$cycloalkyl$(R^q)_3$; $CON(C_{3-8}$cycloalkyl$(R^q)_3)_2$; $CON(C_{3-8}$cycloalkyl)$(C_{1-6}$alkyl$(R^q)_3)$; $CO_2H$; $CO_2$ $C_{1-6}$alkyl$(R^q)_3$; $C(O)C_{1-6}$alkyl$(R^q)_3$; $CO_2$ $C_{3-8}$cycloalkyl$(R^q)_3$; $C(O)C_{3-8}$cycloalkyl$(R^q)_3$; $-[C(O)(CH_2)_j-CR^5R^6-(CH_2)_k-NR^7]_p-R^8$; $-C(O)$heterocyclyl$(R^q)_3$, $-CON[C_{1-6}$alkyl$(R^q)_3]$ $C_{3-8}$cycloalkyl$(R^q)_3]$; $-C(O)$aryl$(R^q)_3$; $-C(O)$heteroaryl$(R^q)_3$; hydroxy; $C_{1-6}$alkyl$(R^q)_3$; $C_{3-8}$cycloalkyl$(R^q)_3$; $OC_{1-6}$alkyl$(R^q)_3$; $OC_{3-8}$cycloalkyl$(R^q)_3$; heterocyclyl$(R^q)_3$; CN; $NH(R^{q''})$; $NHC_{1-6}$alkyl$(R^q)_3$; $N(C_{1-6}$alkyl$(R^q)_3)_2$; $NHC_{3-8}$cycloalkyl$(R^q)_3$; $N(C_{3-8}$cycloalkyl$(R^q)_3)_2$; $CF_3$; SH; $NO_2$; $C_{2-4}$alkenyl$(R^q)_{2-3}$, aryl$(R^q)_3)_2$; heteroaryl$(R^q)_3$; $C_{2-4}$alkynyl$(R^q)_{1-3}$; OC(O) $C_{3-8}$cycloalkyl$(R^q)_3$; $SO_2NH_2$; $SO_2NH$ $C_{1-6}$alkyl$(R^q)_3$; $SO_2N(C_{1-6}$alkyl$(R^q)_3)_2$; NH $SO_2C_{1-6}$alkyl$(R^q)_3$; $NHSO_2$aryl$(R^q)_3$; $NHSO_2$heteroaryl$(R^q)_3$; OC(O)heterocyclyl$(R^q)_3$; $N(R^{q''})C(O)$ $C_{1-6}$alkyl$(R^q)_3$; $NR^{q''}C(O)NH(C_{1-6}$alkyl$(R^q)_3)$; $OC(O)C_{1-6}$alkyl$(R^q)_3$; $-OC(O)$aryl$(R^q)_3$; OC(O)heteroaryl$(R^q)_3$; $-C(=NR^{q''})NH_2$; $-C(=NR^{q''})NH$ $C_{1-6}$alkyl$(R^q)_3$; $-C(=NR^{q''})N(C_{1-6}$alkyl$(R^q)_3)_2$; $-O-[C(O)-(CH_2)_j-CR^5R^6-(CH_2)_k-NR^7]_p-R^8$ and $-[NR^7(CH_2)_k-CR^5R^6-(CH_2)_j-C(O)]_p-OR^9$ wherein j and k independently represent integers of from 0–3;

$R^5$ and $R^6$ are independently H, aryl, $C_{1-6}$alkyl$(R^q)_3$, or $CR^5R^6$ in combination represents a 3, 4, 5 or 6 membered cycloalkyl or heterocyclyl group, an aryl group or a heteroaryl group;

p represents 1, 2 or 3, with the proviso that when p represents 1, $CR^5R^6$ represents a 3, 4, 5 or 6 membered cycloalkyl group or a heterocyclyl group, an aryl group or a heteroaryl group, and at least one of j and k is 1, 2 or 3;

$R^7$ and $R^8$ are independently H, $C_{1-6}$ alkyl or aryl;

$R^9$ represents H, a negative charge balanced by a positively charged group or a protecting group;

$R^q$ represents a member selected from the group consisting of: $R^{q'}$; halo; CN; $CO_2H$; $CO_2$ $C_{1-4}$alkyl; C(O) $C_{1-4}$alkyl; $NH(R^{q''})$; aryl$(R^q)_3$; heteroaryl$(R^q)_3$; $NHC_{1-4}$alkyl; $N(C_{1-4}$alkyl$)_2$; $CONH_2$; SH; $S(O)_y$ $C_{1-6}$alkyl$(R^q)_3$; $C(O)NH$ $C_{1-6}$alkyl $(R^q)_3$; $C(O)N(C_{1-6}$alkyl$(R^q)_3)_2$; $C_{3-8}$cycloalkyl; $NHC(NH)NH_2$; heteroalkyl$(R^q)_3$; $-NHC(O)NH_2$;

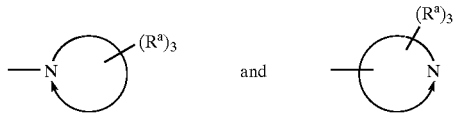

wherein

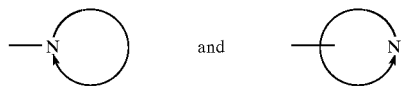

independently represent mono or bicyclic ring systems, non-aromatic or partially aromatic, containing from 5–10 ring atoms, 1–4 of which are N and 0–1 of which are O or $S(O)_y$, with y equal to 0, 1 or 2, optionally containing 1–2 carbonyl groups;

each $R^a$ independently represents a member selected from the group consisting of: H, $C_{1-6}$ alkyl, $OC_{1-6}$ alkyl, aralkyl, substituted aralkyl, heteroaralkyl, substituted heteroaralkyl, aralkoxy, substituted aralkoxy, halo, hydroxy, CN, $CONH_2$, $CONHC_{1-6}$ alkyl, $CON(C_{1-6}$ alkyl$)_2$, $CO_2H$, $CO_2C_{1-6}$ alkyl, $C(O)C_{1-6}$alkyl, phenyl, $CF_3$, SH, $NO_2$, $SO_y$ $C_{1-6}$alkyl, with y as defined above; $SO_2NH_2$, $SO_2NH$ $C_{1-6}$alkyl, NH $SO_2$(substituted aryl), $NHSO_2$(substituted heteroaryl), NH $SO_2C_{1-6}$ alkyl, NH $SO_2$aryl, NH $SO_2$heteroaryl, $NH_2$, $NHC_{1-6}$alkyl, $N(C_{1-6}$alkyl$)_2$, $NHC(O)C_{1-6}$alkyl, NHC(O)NH ($C_{1-6}$alkyl), $C_{2-4}$alkenyl and $C_{2-4}$ alkynyl;

$R^{q'}$ represents H, OH, $C_{1-4}$alkyl, —O $C_{1-4}$alkyl, aryl or C(O) $C_{1-4}$alkyl, and $R^{q''}$ represents H, OH or O $C_{1-4}$alkyl.

2. A method according to claim 1 wherein one or two R" groups are present, and each independently represents $NH_2$, $NHC_{1-6}$alkyl($R^q$)$_3$, $N(C_{1-6}$alkyl$)_2$, $NHC_{3-8}$cycloalkyl, $N(R^{q'})C(O)C_{1-6}$alkyl($R^q$)$_3$, $C_{1-6}$alkyl($R^q$)$_3$, $OC_{1-6}$alkyl($R^q$)$_3$, $CO_2H$, $CONH_2$, $NR^{q'}C(O)NH$ $C_{1-6}$alkyl($R^q$)$_3$ or heterocyclyl($R^q$)$_3$.

3. A method according to claim 1 wherein: HETCy represents a 5–6 membered non-aromatic heterocycle with 1–2 nitrogen atoms contained therein.

4. A method according to claim 1 wherein HETCy represents a pyrrolidinyl or piperidinyl group.

5. A method according to claim 1 wherein R' is selected $C_{1-6}$ alkyl($R^q$)$_3$, $OC_{1-6}$alkyl($R^q$)$_3$, $C(O)CC_{1-6}$ alkyl($R^q$)$_3$; CN, $NO_2$ and $CO_2$ $C_{1-6}$alkyl($R^q$)$_3$.

6. A method according to claim 1 wherein from 1–3 R groups are present and each independently represents a member selected from the group consisting of: halo, hydroxy, $C_{1-6}$alkyl($R^q$)$_3$, $C_{1-6}$alkyl($R^q$)$_3$, $NH_2$, NH $C_{1-6}$alkyl ($R^q$)$_3$, $N(C_{1-6}$alkyl($R^q$)$_3)_2$ and $CF_3$.

7. A method according to claim 6 wherein one or two R groups are present, selected from halo and $CF_3$.

8. A method according to claim 1 wherein $R^x$ is H, $C_{3-8}$cycloalkyl or $C_{1-6}$alkyl($R^q$)$_3$.

9. A method according to claim 8 wherein $R^x$ represents H, $CH_3$, $CH_2CH_3$, $CH_2CH_2CH_3$, $CH_2$ $CH_2CH_2$ $CH_3$,

or

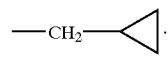

10. A method according to claim 1 wherein X' represents a direct bond.

11. A method according to claim 1 wherein X represents —$(CH_2)_m$—Y—$(CH2)_n$—, Y represents a direct bond, O, S or C(O); m represents 0 or 1 and n represents 0 or 1.

12. A method according to claim 11 wherein X represents a direct bond.

13. The method according to claim 1 wherein the CNS injury is ischemic stroke.

14. The method according to claim 1 wherein the CNS injury is caused by surgery, or is an open head injury.

15. The method according to claim 1 wherein the CNS injury is a closed head injury.

* * * * *